United States Patent [19]

Walker et al.

[11] 4,010,114
[45] Mar. 1, 1977

[54] OXIDATIVE DEHYDROGENATION CATALYST

[75] Inventors: Darrell W. Walker; Floyd E. Farha, Jr., both of Bartlesville, Okla.

[73] Assignee: Phillips Petroleum Company, Bartlesville, Okla.

[22] Filed: Apr. 30, 1975

[21] Appl. No.: 573,210

[52] U.S. Cl. .................. 252/437; 252/435
[51] Int. Cl.² ......................... B01J 27/14
[58] Field of Search ............... 252/435, 437

[56] References Cited

UNITED STATES PATENTS

| | | | |
|---|---|---|---|
| 3,143,490 | 8/1964 | Brennan | 252/437 X |
| 3,687,868 | 8/1972 | Pitzer | 252/437 |
| 3,789,017 | 1/1974 | Walker | 252/437 |
| 3,790,501 | 2/1974 | Walker | 252/437 |
| 3,801,671 | 4/1974 | Marsheck | 252/437 |
| 3,810,953 | 5/1974 | Cichowski | 252/435 X |
| 3,821,324 | 6/1974 | Bertus | 252/435 X |
| 3,845,156 | 10/1974 | Farha | 252/437 |
| 3,864,279 | 2/1975 | Pitzer | 252/437 |

*Primary Examiner*—Winston A. Douglas
*Assistant Examiner*—John F. Niebling

[57] ABSTRACT

Ferrous metal/tin/phosphorus/alkali metal/oxygen-containing oxidative dehydrogenation catalysts are improved by including a small amount of lead; higher yields and higher gas phase selectivities to dehydrogenated products in the oxidative dehydrogenation process are achieved by these novel lead-containing catalysts.

9 Claims, No Drawings

OXIDATIVE DEHYDROGENATION CATALYST

The present invention relates to the oxidative dehydrogenation of organic compounds. More particularly, this invention relates to the oxidative dehydrogenation of isoparaffins.

BACKGROUND OF THE INVENTION

Organic hydrocarbon compounds can be dehydrogenated efficiently by contacting these compounds in the vapor phase in the presence of a free oxygen-containing gas with a catalyst comprising at least one element of the iron group consisting of nickel, cobalt and iron in association with tin, phosphorus and at least one alkali metal and oxygen. By this process, various unsaturated hydrocarbons such as butene, butadiene, isoprene, etc., can be produced from hydrocarbon feedstocks having at least one

grouping. While this process constitutes an important improvement over the earlier procedures for the production of unsaturated hydrocarbon compounds, it remains desirable to increase the yield and selectivity of this process.

THE INVENTION

One object of this invention is to provide new catalysts for the oxidative dehydrogenation process.

Another object of this invention is to provide new catalysts for an oxidative dehydrogenation process with high yield and selectivity.

A further object of this invention is to provide a new process for oxidative dehydrogenation of hydrocarbons.

Still another object of this invention is to provide a new process for the oxidative dehydrogenation of hydrocarbons having high yield and selectivities.

Still a further object of this invention is to provide a process for the production of isoamylenes and isoprene from isopentane with high yield and selectivity.

These and other objects, advantages, details and embodiments of this invention will become apparent to a person skilled in the art from the following detailed description of the invention as well as the appended claims.

In the context of this invention, selectivity is based on the analyses of gas phase products including carbon oxides, cracked products, olefins, paraffins, oxygen and nitrogen. This simplified selectivity is the gas phase selectivity referred to.

In accordance with this invention, we have now found that the yield and selectivity of an oxidative dehydrogenation process employing a catalyst comprising at least one of the elements nickel, cobalt and iron in association with the tin, phosphorus and at least one alkali metal as well as oxygen can be increased by incorporating lead into this catalyst.

The usually employed and preferred ranges for the catalyst elements are given in the following table, the weight percentages being based on the unsupported catalyst as 100 percent.

| Element | Weight Percent Broad | Preferred |
|---|---|---|
| Nickel, Iron or Cobalt | 26–75 | 35–55 |
| Tin | 1–50 | 5–25 |
| Lead | 0.5–10 | 1–6 |
| Phosphorus | 0.5–10 | 2–8 |
| Alkali Metal | 0.5–6 | 0.8–2 |

The percentages shown above are based upon a total weight of the finished catalyst and the difference between the total of the weights of the above named elements and 100 percent is made up by its oxygen content in amounts sufficient to satisfy the valences of each of the elements in the catalyst. Sufficient oxygen is present to satisfy the valence requirements of the elements in the composition. The elements contained in the catalyst form various compounds with oxygen as well as with each other such as nickel stannate, potassium phosphate, lead oxide, sodium stannate, etc.

In accordance with one preferred embodiment of this invention, the catalyst consists essentially of the ingredients given above, namely the metals, the phosphorus and the oxygen without a support being present.

The catalyst of this invention is generally used in the form of solid particles, pellets, wafers or the like. The surface area of the catalyst ranges from about 1 to about 200 square meters per gram, preferably from about 25 to about 175 square meters per gram. The apparent bulk density of the catalyst varies, depending upon the method of preparation. However, the value generally falls within the range of about 0.2 to about 1.0 gram per cubic centimeter.

In accordance with one embodiment of this invention, there is provided a catalyst that is obtained by first preparing a wet gel comprising the ferrous metal component, the tin component and the lead component. The phosphorus component can be added at any stage of the process before the gel is dried. The alkali metal can be added at any stage of the process before calcining. The gel is dried and calcined by contacting it with a free oxygen-containing gas at elevated temperatures.

The lead can be incorporated into the catalyst starting from various water-soluble lead compounds. The presently preferred group of lead compounds consist of lead nitrate, lead acetate, lead citrate, lead formate and lead lactate.

It is presently preferred to coprecipitate the tin compound, the ferrous metal compound and the lead compound in the presence of a suitable alkali metal compound. Alternatively, the ferrous metal compound, the tin compound, and the lead compound can be coprecipitated and the resulting wet gel can be impregnated with an alkali metal compound.

It is particularly convenient and therefore preferred to introduce the alkali metal component during the coprecipitation period. Particularly, it is advantageous to employ an alkali metal stannate compound which serves as source for both the alkali metal and the tin. Thus, potassium stannate, sodium stannate and the like can be used. After the stannate compound has been coprecipitated with the ferrous metal compound and the lead compound, the alkali metal content of the resulting wet gel can be adjusted to a desired level either by water washing if the alkali metal compound is too high or by impregnation with an alkali metal compound if the alkali metal content of the gel is too low.

Depending upon the proportions of tin compound, ferrous metal compound, lead compound and phosphorus compound in the coprecipitation stage, an inorganic base, particularly an alkali metal hydroxide, can be added to maintain a suitable pH of about 7 or higher. This alkali metal hydroxide can provide all or a portion of the desired alkali metal in the finished catalyst.

For the production of the catalyst, substantially any ferrous metal, tin, lead, phosphorus and alkali metal compound can be employed. The only limitation is that the additional components are not detrimental to the catalyst and are removed from the catalyst prior to its end use. In some instances, however, small amounts of some other elements which are involved in the preparation of the catalyst can be tolerated in the final catalytic composition. For example, if a sulfate such as nickel sulfate or tin sulfate is employed in the preparation, small residual amounts of sulfur can be tolerated. Halogen residues, on the other hand, are less desirable in the catalyst. Therefore, the use of the halides, e.g. lead chloride, is less desirable.

Generally, the preferred ferrous metal, tin, phosphorus, lead and alkali metal compounds are either the oxides of these elements or compounds convertible to oxides during the calcination step. Some examples of such compounds are nickel nitrate, cobalt acetate, ferric nitrate, nickel stannate, potassium stannate, stannic chloride, stannous oxalate, phosphoric acid, lead acetate, lead nitrate, potassium hydroxide, rubidium nitrate, sodium carbonate, lithium phosphate, cesium tartrate, and the like and mixtures thereof. The calcination of the precipitated compounds is carried out by contacting these compounds at the temperature of about 900 to about 1400° F (482°–760° C) with a free oxygen-containing gas. Examples of such gases are oxygen, oxygen containing air, air, mixtures of oxygen and carbon oxides and the like. The calcination is usually carried out for 1 to about 24 hours.

In accordance with this invention, hydrocarbons are dehydrogenated by contacting them in the vapor phase with a catalyst as defined above in the presence of oxygen. Preferred feedstocks are acyclic hydrocarbons having 2 to about 12 carbon atoms and at least one

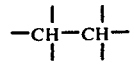

grouping including branched and unbranched paraffins and monoolefins. Examples of such feedstocks are ethane, propane, butane, isobutane, pentane, isopentane, hexane, 2-methylhexane, octane, 2,4-dimethyloctane, dodecane, butene, 2-methylbutene-1, hexene-2, octene-1, 3-methylnonene, dodecene-1, etc. The presently preferred feedstock for the dehydrogenation process of this invention is, however, isopentane. Isopentane is dehydrogenated effectively into isoamylenes and isoprene by contacting the isopentane in the vapor phase and in the presence of a free oxygen-containing gas with the catalyst of this invention defined above and containing a small quantity of lead. One of the outstanding advantages of this process and this catalyst is that the production of the carbon oxides during the oxidative dehydrogenation process is reduced.

The oxidative dehydrogenation process is generally carried out at a temperature in the range of about 800° to about 1300° F. (426°–704° C), preferably in a temperature range of about 950° to about 1200° F (510°–649° C). The process pressure is selected to be a conveniently obtained pressure such as in the range of about 0 to about 250 psia. The molar ratio of oxygen to hydrocarbon is preferably about 1 to 1 to about 4 to 1. The presence of steam is frequently beneficial and this steam can be applied in a molar ratio of steam to hydrocarbon of up to about 50 to 1. The hydrocarbon is generally contacted by the catalyst in a ratio of about 50 to about 5000 volumes of hydrocarbon feed per volume of catalyst per hour. This ratio of the hourly hydrocarbon feed volume to the catalyst volume depends upon the results one wishes to obtain as well as upon the surface area of the catalyst. The larger the surface area of the catalyst in square meters per gram, for instance, the higher the ratio of the volume of hydrocarbon feed per volume of catalyst per hour is, that can be used to obtain otherwise the same results. The catalyst can be used in a fluidized bed form, however, a fixed bed catalyst is the presently preferred mode of carrying out the dehydrogenation process. The volumes referred to in these ratios are measured in the vapor or gas phase and calculated to standard temperature and pressure conditions.

The dehydrogenatable hydrocarbon feed, the oxygen-containing gas and—if used—the steam, are preferably mixed and preheated and then introduced into the reactor containing the catalyst. The effluent from the reaction zone is then subjected to any separation method to isolate and recover the desired products. Unconverted feeds or partially converted materials can be recycled. For example, separation can be achieved by fractional distillation, extractive distillation and the like.

In case the activity of the catalyst has become too low, the catalyst can be regenerated. This regeneration can be conveniently carried out by a calcination step, i.e. by contacting the catalyst with a free oxygen-containing gas under elevated temperatures. The ranges for the temperature and time, as well as the gases used for this calcination, are the same as disclosed above in connection with the calcination step for preparing the oxidative dehydrogenation catalyst.

The invention will be more fully understood from the following examples, which are not intended to limit the scope of the invention.

EXAMPLE I

Preparation of Catalysts a. Control Catalyst A

A first aqueous solution of 300 cc volume was prepared by dissolving 159 grams of Ni(NO$_3$)$_2$.6H$_2$O in water. A second aqueous solution of 150 cc volume was prepared by dissolving 18.5 grams of K$_2$SnO$_3$.3H$_2$O in water and a third aqueous solution of 150 cc volume was prepared by dissolving 75 grams of KOH in water. These three solutions were added simultaneously and dropwise while stirring continuously into 300 cc of distilled water contained in a suitable receptacle while keeping the pH at 8 to 9. The resulting gel was filtered and washed sufficiently to reduce the potassium content in the gel to the desired level of about 1.5 weight percent. The gel then was impregnated with 14.5 grams of phosphoric acid (85 percent H$_3$PO$_4$ diluted with water to 60 cc). The resulting mixture was stirred thoroughly to mix the components, dried in an oven at 230° F. (110° C) and calcined at 700° F. (371° C) for 3 hours in air. After cooling, the resulting material was ground and screened to a material of 20 to 40 (U.S. sieve) (control catalyst A) and fines. The fines were compacted in a hydraulic press, crushed and screened as before to obtain control catalyst A'.

b. Invention Catalyst B

A catalyst sample in accordance with this invention was prepared by essentially repeating the process described above to produce the control catalyst, including, however, 1.8 grams Pb(NO$_3$)$_2$ in the first aqueous solution together with the nickel nitrate. The coprecipitated gel subsequently formed thus contained lead, nickel, tin and potassium. This gel was filtered, washed, impregnated with phosphoric acid, dried, calcined and screened as described above in connection with catalyst A.

The fines were also treated as described to obtain the invention catalyst B'.

c. Invention Catalyst C

Another sample of catalyst in accordance with this invention was prepared by essentially repeating the procedure described above in connection with the control catalyst. This time 4.6 grams of Pb(NO$_3$)$_2$ were dissolved in the first aqueous solution together with the nickel nitrate. The gel was treated as described to result in a catalyst sample C of 20 to 40 mesh (U.S. Sieve) and fines which were compressed, crushed and screened as described to obtain invention catalyst C'.

The compositions of the catalysts as analyzed and their physical properties are presented in Table I.

Table I

| Catalyst No. | Apparent Bulk Density (g/cc) | Surface Area (m²/g) | Composition, Wt. % | | | | | |
|---|---|---|---|---|---|---|---|---|
| | | | Ni | Sn | Pb | P | K | O |
| A | 0.38 | 146 | 48.0 | 10.5 | — | 6.2 | 1.2 | 34.1 |
| B | 0.40 | 155 | 47.8 | 10.5 | 1.7 | 6.3 | 1.1 | 32.6 |
| C | 0.49 | 131 | 45.5 | 9.7 | 4.0 | 5.8 | 1.4 | 33.6 |

EXAMPLE II

Oxidative Dehydrogenation of Isopentane

The catalyst samples A, B and C as prepared in accordance with Example I were individually used in a process for the oxidative dehydrogenation of isopentane in separate runs. The catalyst samples were introduced into reactors in the form of a fixed bed. A preheated gas mixture was formed of gaseous isopentane, oxygen, and steam. The oxygen to isopentane molar ratio was 1.5 and the steam to isopentane molar ratio was 13. This mixed feedstock was passed through the catalyst in the fixed bed reactor at 1075° F (579° C) and at 1,000 GHSV isopentane (gaseous hourly spaced velocity of the isopentane), which means the volume ratio of the isopentane volume per hour per volume of catalyst was 1000, at atmospheric pressure.

The effluent from the reactor was cooled to about room temperature (about 75° F [24° C]) to condense the steam. A sample of the remaining gas was analyzed at about 124° F (51° C) in a Dual Column Analyzer Model 12 commercially available from Applied Automation, Inc. The results of this analysis are shown in the following Table II. In this table, conversion percent refers to the percentage of the isopentane fed which was converted into other compounds. Selectivity is the gas phase selectivity which shows how many mol percent of the desired isoamylenes/isoprene product are in the gas phase based on 100 mols of converted feed in the gas phase. Thus, a selectivity value of 54 percent for isoamylenes/isoprene means that for every 100 mols of isopentane having produced the gas phase during the process 54 mols of the desired products in the gas phase are obtained.

Table II

| Catalyst No. | Conversion % | Selectivity | Yields[a] Isoamylenes Plus Isoprene |
|---|---|---|---|
| A | 19 | 46 | 8.7 |
| B | 17 | 54 | 9.1 |
| C | 17 | 66 | 10.9 |

[a] In mols per 100 mols isopentane fed into reaction zone.

The results of the above shown Table II show that the selectivity and the yields of the dehydrogenation process using the catalyst of this invention (catalysts B and C) are improved as compared to known control catalyst A.

EXAMPLE III

Oxidative Dehydrogenation of Isopentane

Isopentane in this example was oxidatively dehydrogenated using individually catalysts A', B' and C' as prepared in accordance with Example I from the fines. Catalyst was introduced into a fixed bed reactor as described which was operated at atmospheric pressure. The feedstock was a mixture of gaseous isopentane, oxygen and steam. The oxygen to isopentane mol ratio was 1.6 and the steam to isopentane mol ratio was 12. The feedstock was preheated and fed through the catalyst at a temperature of 1050° F (566° C) and at a rate of 1000 GHSV as defined above in connection with Example II.

The effluent of the reactor was again analyzed as described in connection with Example II. The catalyst in this example had a higher apparent bulk density as can be seen by comparing the respective values of Table III with the respective values in Table I.

Table III

| Catalyst No. | Apparent Bulk Density (g/cc) | Conversion % | Selectivity | Yields Isoamylenes Plus Isoprene |
|---|---|---|---|---|
| A' | 0.73 | 25 | 53 | 13.3 |
| B' | 0.78 | 27 | 54 | 14.7 |
| C' | 0.78 | 25 | 62 | 15.3 |

In this example, too, the yield and selectivity achieved by using the catalyst B' and C' of this invention were increased as compared to the control catalyst A'.

Reasonable variations and modifications which will be apparent to those skilled in the art can be made in this invention without departing from the spirit and scope thereof.

We claim:

1. An oxidative dehydrogenation catalytic material consisting essentially of from about 26 to about 75 weight percent of nickel, in association with from about 1 to about 50 weight percent of tin, from about 0.5 to about 10 weight percent of lead, from about 0.5 to about 10 weight percent of phosphorus, from about 0.5 to about 6 weight percent of potassium, and sufficient oxygen to satisfy the valence requirements of the elements, wherein the weight percent values are based on weight of the unsupported catalytic material and wherein at least one of said nickel, said tin, said phosphorus or said potassium is combined with oxygen.

2. A catalytic material in accordance with claim 1 consisting essentially of about 35 to about 55 weight percent of nickel, about 5 to about 25 weight percent of said tin, about 1 to about 6 weight percent of said lead, about 2 to about 8 weight percent of said phosphorus, about 0.8 to about 2 weight percent of said potassium and sufficient oxygen being present to satisfy the stoichiometric requirements of the metal components.

3. A catalytic material in accordance with claim 1 consisting essentially of 47.8 weight percent of nickel, 10.5 weight percent of tin, 1.7 weight percent of lead, 6.3 weight percent of phosphorus, 1.1 weight percent of potassium and 32.6 weight percent of oxygen.

4. A catalytic composition in accordance with claim 1 consisting essentially of about 45.5 weight percent of nickel, about 9.7 weight percent of tin, about 4.0 weight percent of lead, about 5.8 weight percent of phosphorus, about 1.4 weight percent of potassium, and about 33.6 weight percent of oxygen.

5. A catalytic composition in accordance with claim 1 obtained by
   a. coprecipitating nickel in combination with lead and tin from an aqueous precipitation mixture such as to form a wet gel comprising precipitated material,
   b. adding a phosphorus compound prior to a drying of said wet gel,
   c. adding potassium prior to calcining said gel,
   d. calcining said precipitated material containing phosphorus and potassium by heating it in contact with a free oxygen-containing gas, such as to obtain a calcined material.

6. A catalytic composition in accordance with claim 5 wherein at least a portion of said potassium is incorporated into said precipitating solution in the form of a water-soluble inorganic potassium compound.

7. A catalytic composition in accordance with claim 6 wherein said phosphorus is included in said calcined material by impregnating said wet gel with an aqueous orthophosphoric acid solution.

8. A catalytic composition in accordance with claim 6 obtained by
   a. preparing a first aqueous solution by dissolving a nickel salt and a lead salt in water,
   b. preparing a second aqueous solution by dissolving potassium stannate in water,
   c. preparing a third aqueous solution by dissolving potassium hydroxide in water,
   d. simultaneously adding said three aqueous solutions while stirring into water thus forming said aqueous precipitation mixture from which said gel precipitates,
   e. impregnating said gel with aqueous orthophosphoric acid solution,
   f. drying said impregnated gel,
   g. crushing said dried gel and
   h. calcining said crushed gel in contact with air at elevated temperatures.

9. A catalytic composition in accordance with claim 8 wherein said nickel salt is nickel nitrate, and said lead salt is lead nitrate.

* * * * *